United States Patent
Nace

(10) Patent No.: US 8,308,669 B2
(45) Date of Patent: Nov. 13, 2012

(54) KNEE ORTHOSIS WITH HINGED SHIN AND THIGH CUFF

(76) Inventor: Richard A. Nace, Miami, FL (US)

(*) Notice: Subject to any disclaimer, the term of this patent is extended or adjusted under 35 U.S.C. 154(b) by 151 days.

(21) Appl. No.: 12/469,671

(22) Filed: May 20, 2009

(65) Prior Publication Data

US 2009/0292229 A1 Nov. 26, 2009

Related U.S. Application Data

(60) Provisional application No. 61/054,516, filed on May 20, 2008.

(51) Int. Cl.
*A61F 5/00* (2006.01)
(52) U.S. Cl. ......................................................... 602/16
(58) Field of Classification Search .................. 602/16; 601/5
See application file for complete search history.

(56) References Cited

U.S. PATENT DOCUMENTS

| | | | |
|---|---|---|---|
| 4,503,846 A * | 3/1985 | Martin ............................ | 602/16 |
| 4,865,024 A | 9/1989 | Hensley et al. | |
| 4,991,571 A | 2/1991 | Kausek | |
| 5,230,695 A | 7/1993 | Silver et al. | |
| 5,415,625 A * | 5/1995 | Cassford et al. ................ | 602/26 |
| 5,514,081 A * | 5/1996 | Mann ............................... | 602/20 |
| 5,520,622 A * | 5/1996 | Bastyr et al. .................... | 602/16 |
| 5,542,911 A | 8/1996 | Cassford et al. | |
| RE37,209 E * | 6/2001 | Hensley et al. ................. | 602/26 |
| 6,527,733 B1 * | 3/2003 | Ceriani et al. .................. | 602/16 |
| 7,048,704 B2 * | 5/2006 | Sieller et al. .................... | 602/16 |
| 7,410,472 B2 * | 8/2008 | Yakimovich et al. ........... | 602/16 |
| 7,608,051 B1 * | 10/2009 | Nace ................................. | 602/16 |
| 2005/0240135 A1 | 10/2005 | Hoffmeier et al. | |

* cited by examiner

*Primary Examiner* — Patricia Bianco
*Assistant Examiner* — Raymond E Harris
(74) *Attorney, Agent, or Firm* — Larson & Larson, P.A.; Frank Liebenow; Justin P. Miller

(57) ABSTRACT

A knee orthosis has two vertical struts positioned on opposed sides of a knee joint in a generally parallel relationship. Each vertical strut has a hinge member located at a general middle portion; each vertical strut has a top and bottom end portion. An upper thigh cuff attaches at opposed ends to the upper end portions of the two vertical struts whereas a lower shin cuff attaches at opposed ends to the lower end portions. The lower shin cuff has a pair of hinges located proximal to the shin cuff opposed ends for permitting the shin cuff to pivot downwardly away from a shin of a person wearing the knee orthosis. An alternate embodiment employs hinges located proximal to the thigh cuff opposed ends for permitting the thigh cuff to pivot upwardly away from a thigh of a person when the same motion is performed.

14 Claims, 8 Drawing Sheets

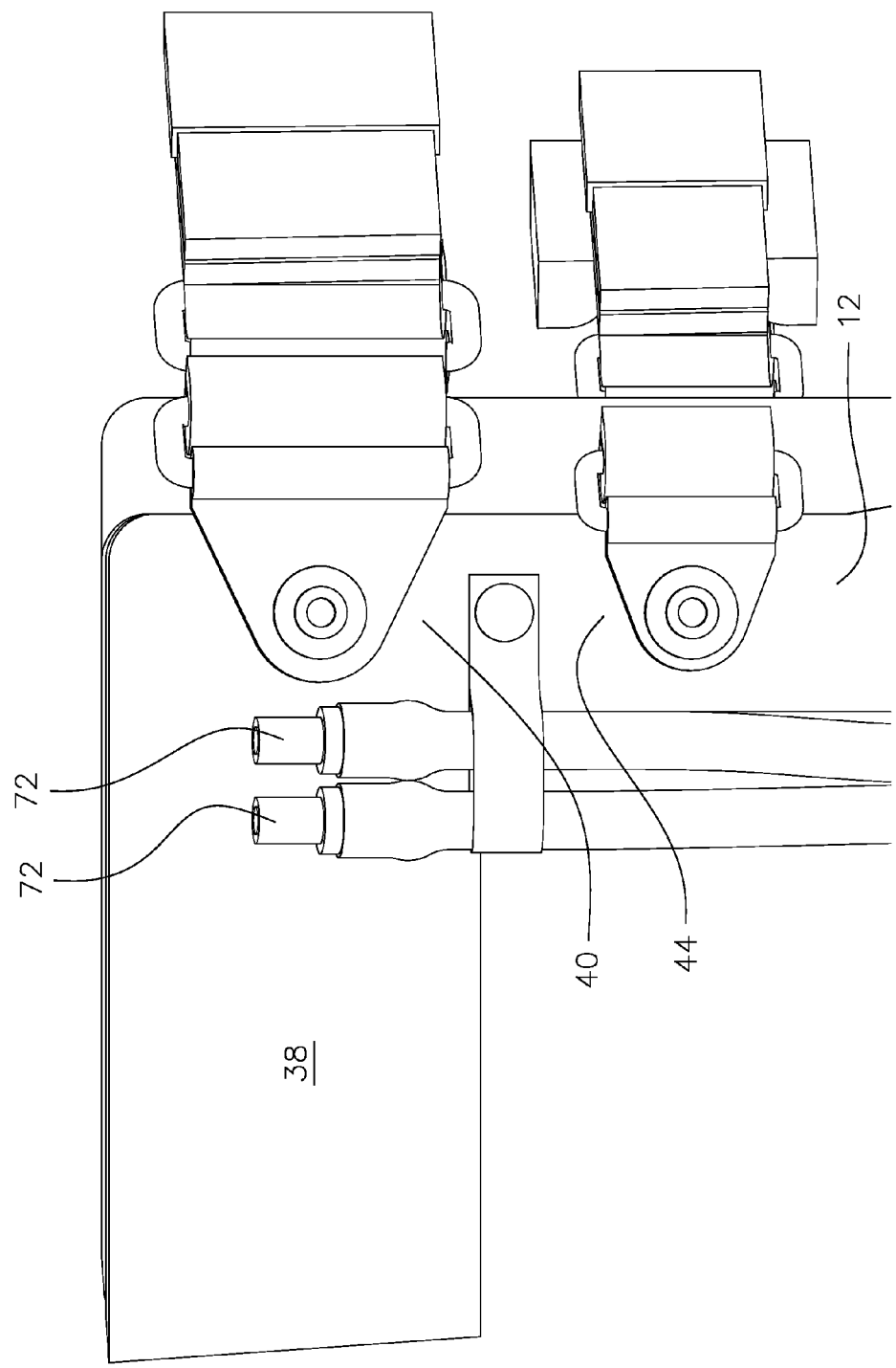

KNEE ORTHOSIS WITH HINGED SHIN AND THIGH CUFF

PRIOR APPLICATIONS

This is a non-provisional patent application that claims priority to provisional patent application 61/054,516, filed May 20, 2008.

FIELD OF THE INVENTION

The invention relates to a knee orthosis. More particularly, it refers to pre-operative, post operative knee orthosis for stabilizing a knee joint of a person before or after surgery or after injury thereto, that applies an adjustable corrective and therapeutic force to the knee joint and surrounding muscles above and below the knee and which also removes pressure from a lower shin cuff of the knee orthosis when a patient using the novel knee orthosis of this present invention flexes the knee joint or performs a body squatting motion through rotation about a shin cuff hinge.

BACKGROUND OF THE INVENTION

Orthosis devices and appliances commonly referred to as "orthotics," are known in the prior art and have been utilized for many years by orthotists (a maker and fitter of orthotics), physical therapists, and occupational therapists to assist in the rehabilitation of a patient's joints and associated limbs or adjacent skeletal parts of the patient's body related to a variety of conditions. An early example can be seen in U.S. Pat. No. 3,581,741 to Rosman, which discloses a knee brace comprising an upper rigid body portion and a lower rigid body portion pivotably coupled together on the lateral side in a manner so that they may pivot relative to each other about an axis generally perpendicular to the zone of overlap and may slide relative to each other in all radial directions generally parallel to the zone of overlap.

Webster's New College Dictionary defines "orthotics" as a branch of mechanical medical science that deals with the support and bracing of weak or ineffective joints or muscles. The word "ortho" actually comes from Greek and means "to straighten." Orthotics are used to support, straighten and stabilize effected joints and assist to correct normal human function as closely as possible. Orthotics used as knee braces have typically been designed to support and protect the knee joint that is associated with a variety of knee joint conditions, for alleviating pain associated with joint movement at the particular location being treated or for immobilizing the knee joint so that movement thereof in either the medial or lateral directions or rotation of the knee is eliminated or at least significantly reduced.

Repetitive use of a joint, such as the knee, over time tends to reduce the stability of the knee. In cases of injury through accident or sports related causes, instability of the knee can be exacerbated and worsened to the point that without immobilization or support of the knee joint by an orthotic, a person can not bare the weight or their own body upon the knee joint. Or to do so, results in great pain, which is usually treated with pain medications that can be addictive and hard on the liver and other important organs of the body. Further, when there is a lack of movement of a patient due to knee instability, a sedentary lifestyle is usually taken up, which can result in a reduction of body energy, weight gain, atrophied muscles, especially around the knee joint, and a general depression of mental state due to the lack of ability of the person to be self-sufficient and mobile.

Therefore, it can be plainly seen that knee orthotics of all types are useful if they assist a person in returning to a more normal lifestyle or at least one that is significantly less sedentary when compared to the immobile person with an instable knee. It can be said that proper use of the knee joints is essential to complete body health and a proper state of mind.

It is well known, as complains are abundant, that not all knee orthotics or braces that stabilize the knee are comfortable to wear. In fact, most apply unwanted pressures upon the thigh and the shin of the patient when the patient walks, squats or flexes the knee joint. This is because all prior art knee orthotics are typically made from very hard and rigid materials that do not flex and move with the changing conditions of the body (i.e., expansion and contraction of the leg musculature), which includes the knee joint area and the upper and lower leg when the patient is walking, flexing, or squatting. This can be particularly seen with the shin cuff that applies a great amount of pressure against the shin of the patient when the patient squats. This therefore discourages the patient from performing any squatting action, which in turns encourages the patient to remain sedentary and results in the degradation of the physical and mental state.

Further, prior art knee orthotics do not employ therapeutic and corrective forces to the knee joint area and the surrounding leg musculature area. Such is needed in combination with a flexible and pliable brace that incorporates a system for reducing or eliminating pressure placed against the shin of the patient when the patient walks or flexes the knee joint or when he squats his body. This can also include alone or together a system for reducing or eliminating pressure placed against the thigh of the patient when the patient walks or flexes the knee joint or when he squats his body. The specific elements that accomplish such pressure elimination include, in the present invention, flexible and pliable materials for both or just one of either the shin or thigh cuffs and hinged shin and thigh cuffs that permit rotation from a 90 degree position to a degree of at least 45 degrees, if nor further.

SUMMARY OF THE INVENTION

The knee orthosis of the present invention provides all of the advantages needed, which are mentioned above and which are currently deficient and wholly missing from the prior art. The present knee orthosis is used and indicated for increased medial, lateral, and rotational support and control of the knee joint following injury to or reconstruction of the anterior cruciate ligament (ACL) and posterior cruciate ligament (PCL) or protection of the collateral ligament of the knee. The present invention provides increased support for patients who have continued symptoms of significant knee instability such as giving way, which may be due to poor quadriceps or hamstring strength (i.e., hemiplegia), or for patients who have a desire for early resumption of activities after knee surgery. The present knee orthosis is also useful after total knee replacement or high tibia osteotomy.

To provide the above set forth benefits and improvements over the prior art, the present knee orthosis device includes two vertical struts, positioned on opposed sides of a knee joint in a generally parallel relationship, wherein each vertical strut has a hinge member located at a general middle portion thereof, and further wherein each vertical strut has a top and bottom end portion. Both polycentric and uni-centric hinges can be employed for the two hinges members, in any combination thereof. An upper thigh cuff attached at opposed ends to the upper end portions of the two vertical struts provides a means to secure the knee orthosis to the thigh of the patient. A secondary thigh strap is also employed to provide additional securing means and is positioned slightly below the thigh cuff. The thigh cuff is positioned posterior to the thigh, whereas the secondary thigh strap and a strap used to secure the thigh cuff are both positioned anterior to the thigh of the patient.

A shin cuff attaches at opposed ends to the lower end portions of the two vertical struts and is positioned anterior to the shin. The shin cuff has a strap member which wraps around the back of the shin of the patient for securing it to the patient's shin. A secondary shin strap is positioned slightly above the shin cuff but is positioned on the posterior side of the shin area of the patient.

The lower shin cuff has a pair of hinges located proximal to the shin cuff opposed ends and left and right vertical strut lower end portions for permitting the shin cuff to pivot downwardly away from a shin of a person wearing the knee orthosis when a person flexes the knee or performs a squatting motion thereby reducing or eliminating unwanted pressure that is usually applied to the shin of a patient of a person when they flex the knee, walk or squat. The shin cuff can pivot upwards of 60-75 degrees.

The novel knee orthosis of the present invention also employs a plurality of air bladders used as therapeutic and corrective force elements for the device. The air bladders are removeably positionable along inner surfaces of the two vertical struts and hinges. Anywhere from one to six air bladders can be employed such that force can be applied on both sides of the knee joint, at the knee joint, directly above the knee joint on the inner and outer thigh area and directly below the knee joint on the inner and outer shin area. When employed they also provide additional stabilization to the knee, prevent brace slippage and provide an extra degree of comfort to patient.

The novel knee orthosis also employs elastic thigh and cuff cushion members positioned along the inner surfaces of the thigh and shin cuff, respectively, for providing more comfort and support. The elasticity of these cushions allows them to bend and flex with the movements of the patient but return to their stable positions after movement by the patient such that the patient's knee joint is continuously stabilized regardless of the movement made by the patient using the knee orthosis of the present invention.

In a first alternate embodiment, the upper thigh cuff also has a pair of hinges located proximal to the thigh cuff opposed ends and left and right vertical strut upper end portions for permitting the thigh cuff to pivot upwardly away from a thigh of a person wearing the knee orthosis when a person flexes the knee or performs any other motion thereby reducing or eliminating unwanted pressure that is usually applied to the thigh of a patient of a person when they flex the knee, walk or squat. The thigh cuff can pivot upwards of 60-75 degrees or more.

BRIEF DESCRIPTION OF THE DRAWINGS

This invention can be best understood by those having ordinary skill in the art by reference to the following detailed description, when considered in conjunction with the accompanying drawings in which:

FIG. 8 illustrates the inflation tubes of the air bladders used in conjunction with knee orthosis of the present invention as the therapeutic and corrective force employed to the knee joint area and the surrounding leg musculature.

DETAILED DESCRIPTION OF THE INVENTION

Figure 1:
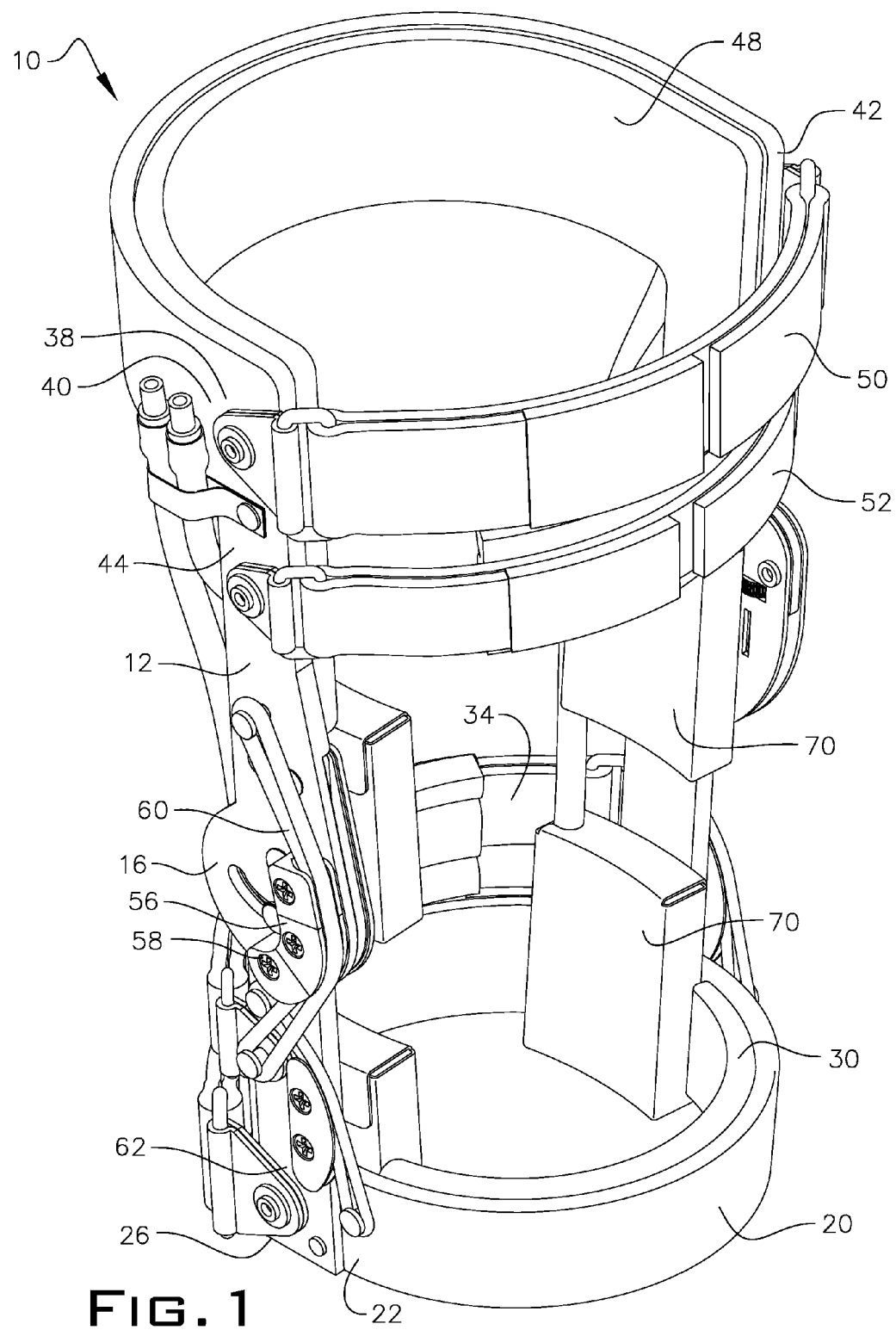
FIG. 1 is a left side perspective view of the knee orthosis of the present invention.

Throughout the following detailed description the same reference numerals refer to the same elements in all figures.

Figure 2:
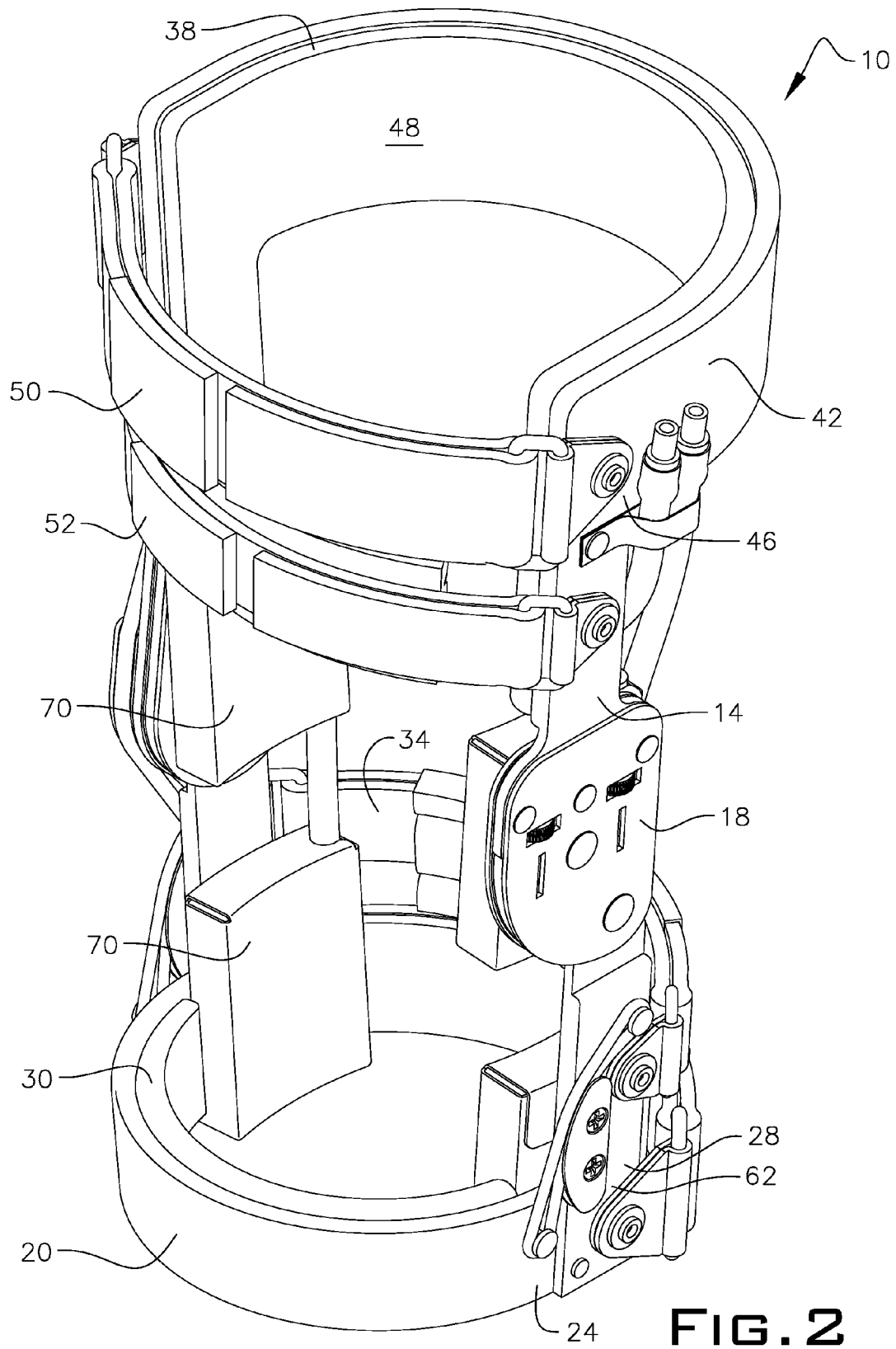
FIG. 2 is a right side perspective view of the knee orthosis of the present invention.

Referring to FIGS. 1 and 2, a knee orthosis 10 of the present is shown. As shown, knee orthosis 10 has a left side and right side vertical strut, 12 and 14, respectively. Struts 12 and 14 are generally parallel and when knee orthosis 10 is employed on a patient run along medial and lateral sides of a knee joint and thigh and shin area of the patient. Each strut has its own hinge 16 and 18 positioned intermediate top and bottom portions of struts 12 and 14 such that knee orthosis 10 pivots about said hinges when the knee joint of the patient is flexed. In the embodiment shown in FIGS. 1 and 2, hinge 16 is a polycentric hinge and hinge 18 is a uni-centric hinge. However, nothing herein limits the use of knee orthosis to this embodiment shown and described herein in this preferred embodiment. In fact, any combination of hinges could be employed.

Figure 3:
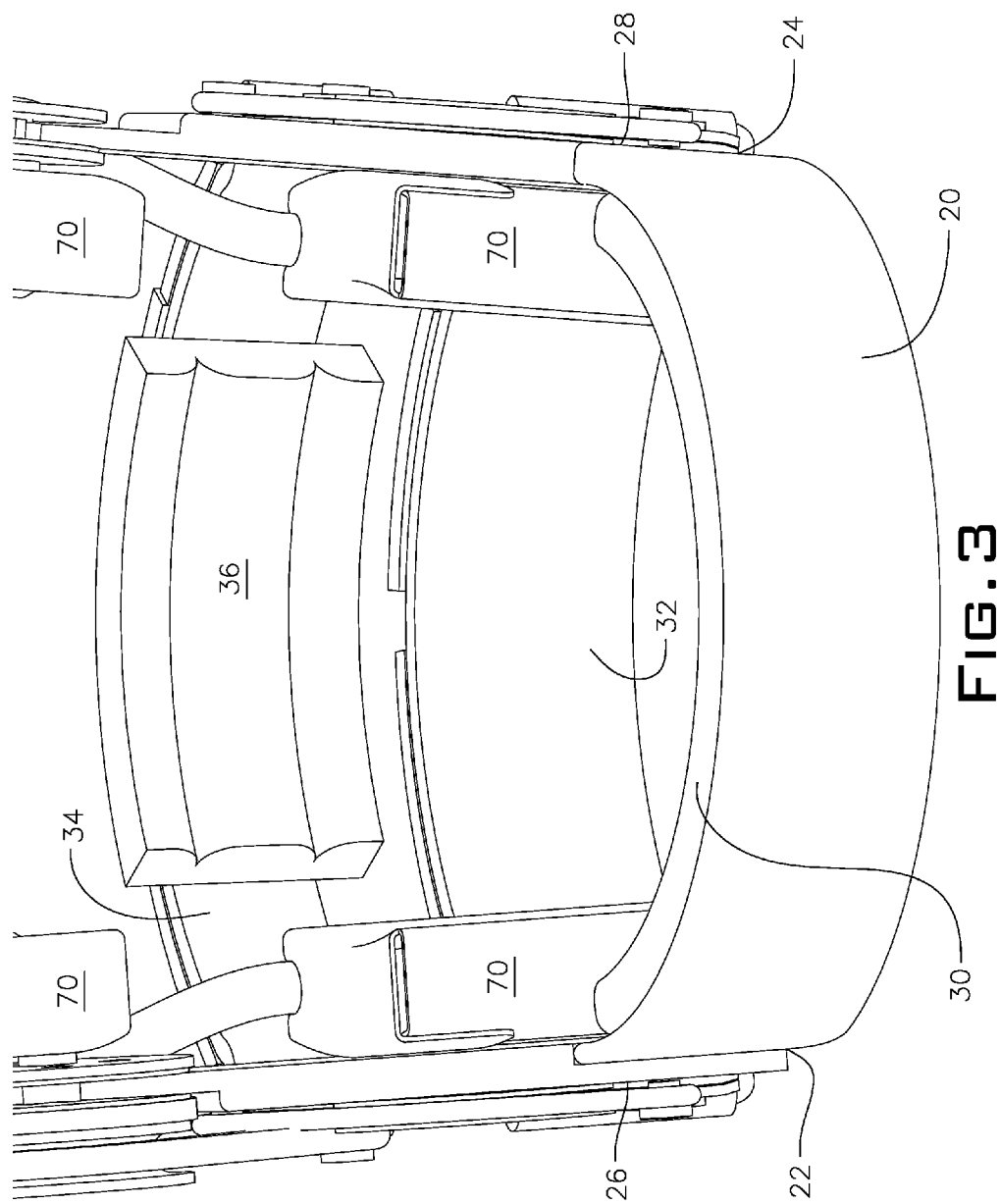
FIG. 3 is a front view of the knee orthosis of the present invention illustrating the shin cuff located at a lower end of the knee orthosis.

Referring to FIG. 3, and also with continuing reference to FIGS. 1 and 2, an anterior positioned shin cuff 20 is shown which has opposed ends 22 and 24. Shin cuff opposed ends 22 and 24 attach to lower ends 26 and 28 of left and right side vertical struts 12 and 14. Attached along an inner surface (not shown) of shin cuff 20 is a flexible shin cushion pad 30 which is removeably attached to said shin cuff 20 inner surface. Shin cuff cushion 30 is very pliable, whose shape is capable of being manipulated and then able to return to its normal resting state, as shown in FIG. 3. It is attached to shin cuff 20 inner surface by hook and loop material.

With continuing reference to FIG. 3, it is shown that shin cuff 20 has a shin cuff strap 32 which wraps behind the shin of a patient for securing thereto. Further, a secondary shin strap 34, with a positionable cushion pad 36, is positioned slightly above shin cuff strap 32 and is used to provide extra securing means for the knee orthosis 10 to the patient. Both shin cuff strap 32 and secondary shin strap 34 each have opposed ends which loop through D-rings (see FIGS. 5 and 6) and then attach to themselves by hook and loop material.

Figure 4:
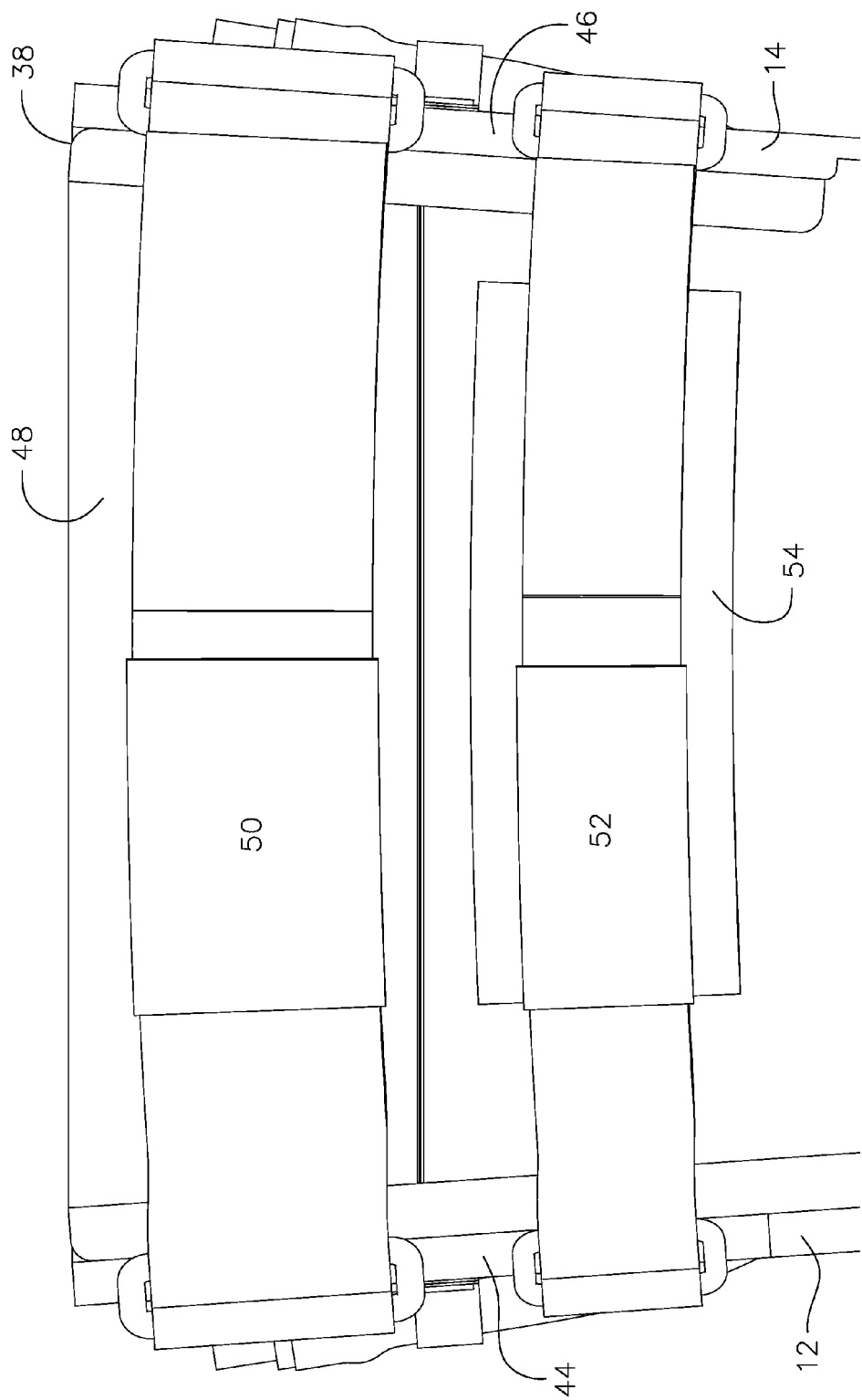
FIG. 4 is a front view of the knee orthosis of the present invention illustrating the thigh cuff located at an upper end of the knee orthosis.

Referring now to FIG. 4, and also with continuing reference to FIGS. 1 and 2, a posterior thigh cuff 38 is shown which has opposed ends 40 and 42. Thigh cuff opposed ends 40 and 42 attach to upper ends 44 and 46 of left and right side vertical struts 12 and 14. Attached along an inner surface (not shown) of thigh cuff 38 is a flexible thigh cushion pad 48 which is removeably attached to thigh cuff 38 inner surface. Thigh cuff cushion pad 48 is very pliable, whose shape is capable of being manipulated and then able to return to its normal resting state, as shown in FIG. 4. It is attached to thigh cuff 38 inner surface by hook and loop material.

With continuing reference to FIG. 4, it is shown that thigh cuff 38 has a thigh cuff strap 50 which wraps in front of the thigh of a patient for securing thereto. Further, a secondary thigh strap 52, with a positionable cushion pad 54 is positioned slightly below thigh cuff strap 50 and is used to provide extra securing means for the knee orthosis 10 to the patient. Both thigh cuff strap 50 and secondary thigh strap 52 each have opposed ends which loop through D-rings (see FIGS. 1 and 2) and then attach to themselves by hook and loop material.

Figure 5:
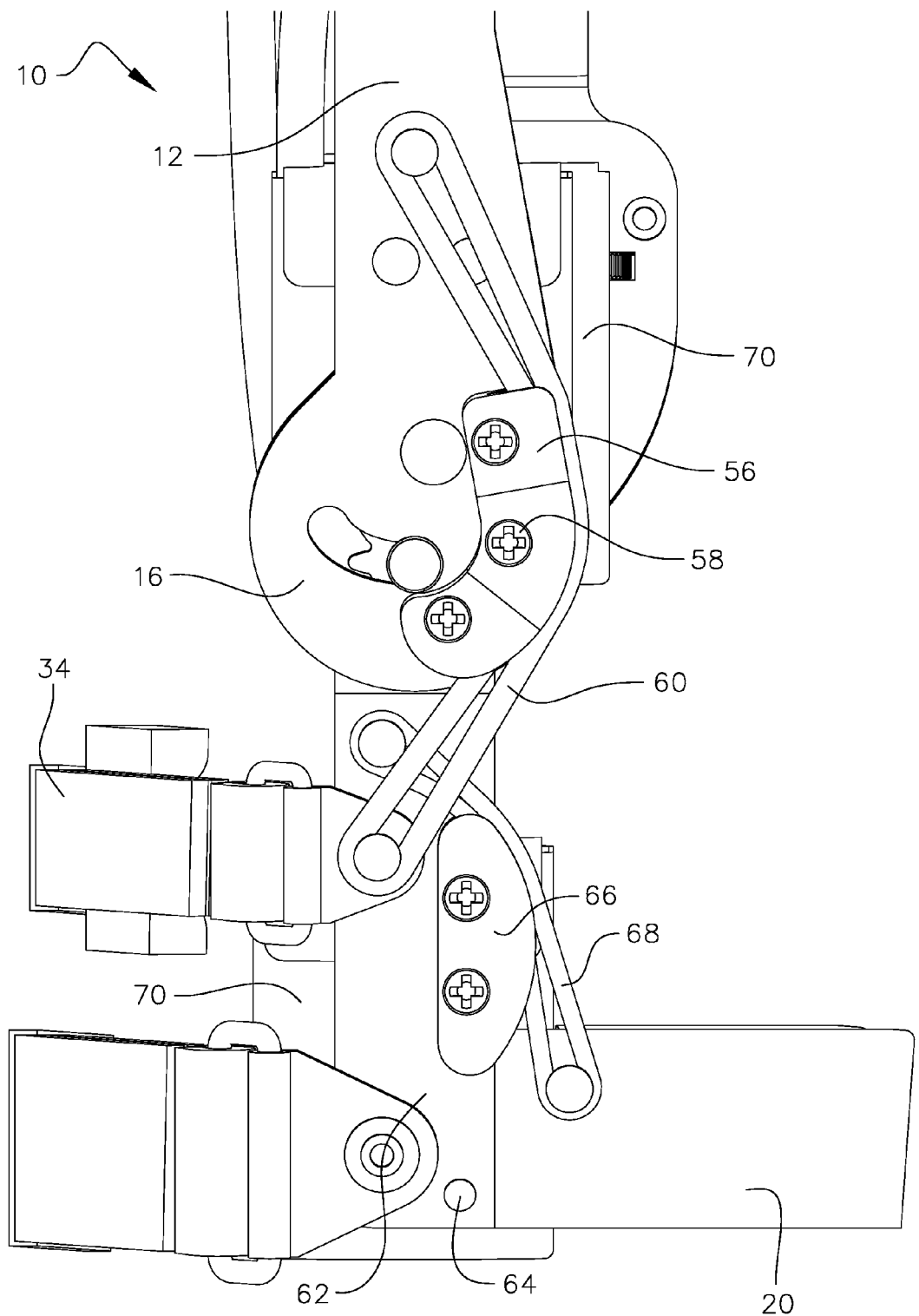
FIG. 5 is a left side view of the knee orthosis of the present invention illustrating a polycentric hinge and dynamic fulcrum of a left side vertical strut and a left side shin cuff hinge.

Referring now to FIG. 5, it is shown that polycentric hinge 16 includes a dynamic fulcrum 56, which includes a plurality of setting blocks 58 and an elastic cord 60, attached at opposed ends to knee orthosis 10, and stretching over the plurality of setting blocks 58 for providing a swing assist assembly to knee orthosis 10 to assist patients in gait kinetics and musculature exercise. Nothing herein limits the use of only one dynamic fulcrum 56, nor does anything herein limit which side fulcrum 56 is employed in the case that only one fulcrum 56 is employed with knee orthosis 10 as shown in the preferred embodiment.

Figure 6:
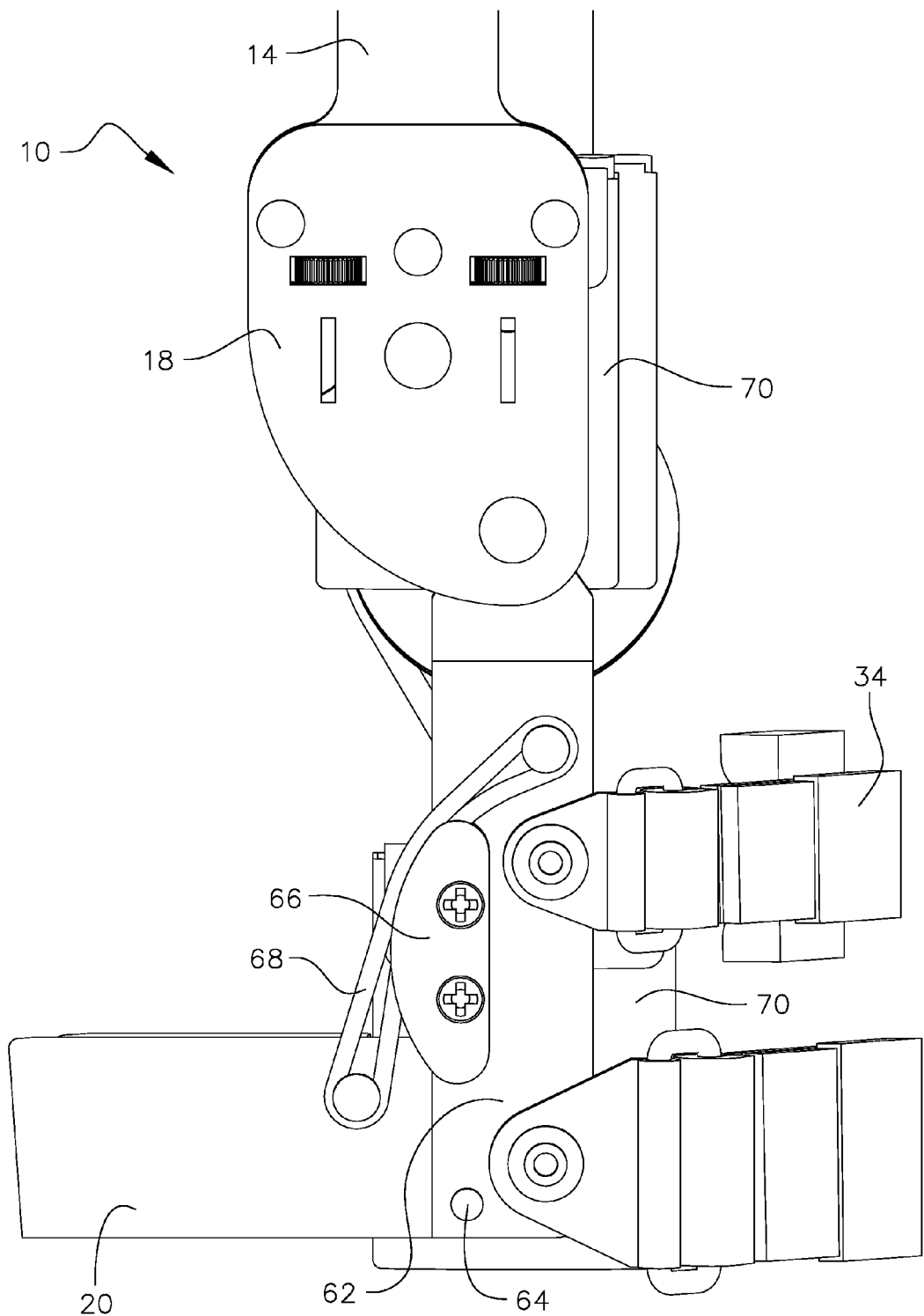
FIG. 6 is a right side view of the knee orthosis of the present invention illustrating a uni-centric hinge and of a right side vertical strut and a right side shin cuff hinge.
Figure 7:
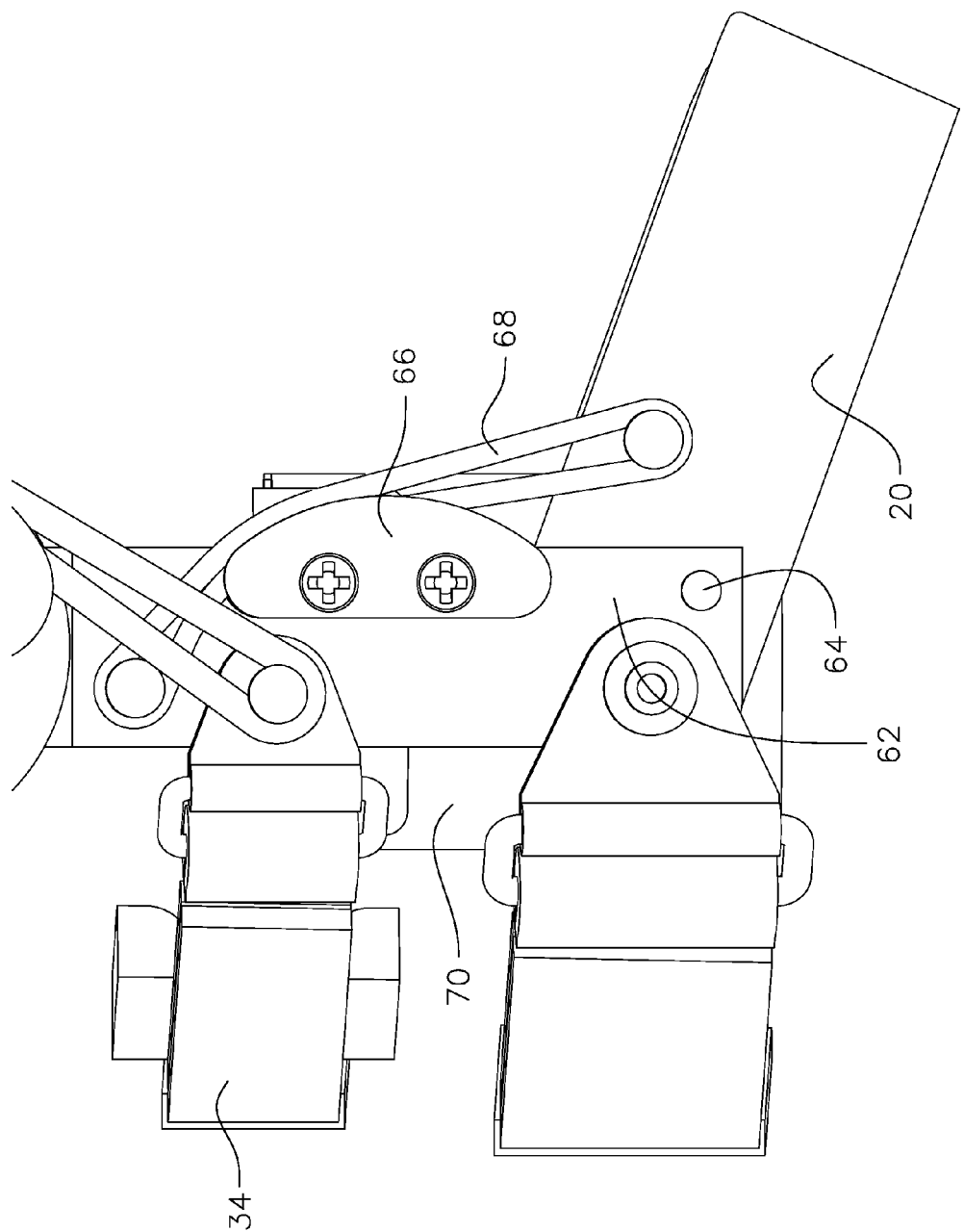
FIG. 7 is a left side view of the knee orthosis of the present invention illustrating how the shin cuff angles downwardly away from a horizontal plane.

Referring now to both FIGS. 5 and 6, it is shown that knee orthosis 10 also includes a shin cuff hinge assembly 62 on both left and right lower ends, 26 and 28, of left and right vertical struts, 12 and 14. Each shin cuff hinge assembly 62 contains a pivoting axis 64, a setting block 66 and an elastic cord 68, attached at opposed ends to knee orthosis 10, for stretching over setting block 66. As shown in FIG. 7, shin cuff 20 pivots downwardly about both axis 64, so that shin cuff 20 reduces the pressure applied against the shin of the patient when he walks, flexes his knee or squats down. Elastic cords 68 provide a means to return shin cuff 20 to its normal resting state when the patient ceases to walk, flex his knee or squat down.

Referring back to FIGS. 1 and 2, it can be seen that a plurality of air bladders 70 are employed along inner surfaces of the left and right vertical struts 12 and 14. Bladders 70 are attached to knee orthosis 10 by hook and loop material and are therefore removeably attachable. Although only four air bladders 70 are shown, nothing herein limits the use of more or less than four bladders. For example, in an alternate embodiment, six air bladders 70 are employed to provide corrective and therapeutic force to the knee joint area at the knee joint on both sides, above the knee joint on both sides and below the knee joints on both sides.

Referring to FIG. 8, a set of inflation tubes 72 are shown, which are used to inflate or deflate air bladders 70 depending on therapist or patient preferences.

In the preferred embodiment, knee orthosis 10 is made from highly pliable, semi-rigid materials that permit knee orthosis 10 to bend, flex and move with the movements of the patient, but all the while maintaining the knee in a completely stabilized and immobile state. However, nothing herein limits the use of more rigid, less pliable materials if necessary.

Although not shown, the upper thigh cuff can also employ a pair of hinges located proximal to the thigh cuff opposed ends and left and right vertical strut upper end portions for permitting the thigh cuff to pivot upwardly away from a thigh of a person wearing the knee orthosis when a person flexes the knee or performs any other motion thereby reducing or eliminating unwanted pressure that is usually applied to the thigh of a patient of a person when they flex the knee, walk or squat. The thigh cuff can pivot upwards of 60-75 degrees or more. The present invention can employ a hinged shin cuff, a hinged thigh cuff or both a hinged shin and thing cuff.

Other equivalent elements can be substituted for the elements disclosed herein to achieve the same results in the same way and in the same manner.

Having thus described the invention, what is claimed for Letters Patent follows:

1. A knee orthosis device comprising:
   a) two vertical struts, positioned on opposed sides of a knee joint in a generally parallel relationship, each vertical strut having a hinge member located at a general middle portion thereof each vertical strut, each vertical strut having a proximal half and a distal half, the proximal half having a proximal end, the distal half having a distal end;
   b) an upper thigh cuff attached at opposed ends to the proximal ends of the two vertical struts;
   c) a lower shin cuff attached at opposed ends to the distal ends of the two vertical struts;
   d) a swing assist assembly containing at least one elastic member located on one or both of the hinge members, the at least one elastic member connected on a first end to the proximal half of each of the two vertical struts and connected on a second end to the distal half of each of the two vertical struts; and
   e) one or more interchangeable setting blocks, the one or more interchangeable setting blocks affecting the tension of the at least one elastic member.

2. The knee orthosis of claim 1, further comprising at least one air bladder employed along an inner surfaces of one or both of the vertical struts.

3. The knee orthosis of claim 1 further comprising a plurality of air bladders employed along an inner surface of one or both of the vertical struts, the plurality of air bladders configured to apply corrective and therapeutic force to the knee joint.

4. The knee orthosis of claim 1, wherein the lower shin cuff is rotatable about the pair of pivots, thereby allowing an inner surface of the lower shin cuff to remain substantially parallel to a shin of a person wearing the knee orthosis during motion.

5. A knee orthosis device comprising:
   a) two vertical struts, positioned on opposing; sides of a knee joint in a generally parallel relationship, each of the two vertical struts having a proximal half and a distal half, each proximal half having a first end and second end, each distal half having a third end and forth end;
   b) each of the two vertical struts having a hinge member, each hinge member connecting its respective second and third ends;
   opposed ends of an upper thigh cuff attached to each of the two vertical struts at a point adjacent to the first ends of each of the two vertical struts;
   d) opposed ends of a lower shin cuff attached to each of the two vertical struts at a point adjacent to the fourth ends of each of the two vertical struts; and
   e) at least one elastic member connected at one end to the proximal half of each of the two vertical struts and connected on a second end to the distal half of each of the two vertical struts; and
   f) one or more interchangeable setting blocks, the one or more interchangeable setting blocks affecting the tension of the at least one elastic member.

6. The knee orthosis of claim 5 further comprising a plurality of adjustable air bladders employed along an inner surface of one or both of the vertical struts, the adjustable air bladders configured to apply varying amounts of corrective and therapeutic force to the knee joint, the varying amounts of force adjustable based on air pressure.

7. The knee orthosis of claim 5, wherein the lower shin cuff is attached at opposite ends to each of the vertical struts by a pair of pivots, each pivot of the pair of pivots located at the fourth end of each of the vertical struts.

8. The knee orthosis of claim 5, wherein the lower shin cuff is rotatable about the a pair of pivots, thereby allowing an inner surface of the shin cuff to remain substantially parallel to a shin of a person wearing the knee orthosis during motion.

9. A knee orthosis device comprising:
 a) two vertical struts, positioned on opposed sides of a knee joint in a generally parallel relationship, each vertical strut having a hinge member located at a general middle portion thereof each vertical strut, each vertical strut having a proximal half and a distal half, the proximal half having a proximal end, the distal half having a distal end;
 b) an upper thigh cuff attached at opposed ends to the proximal ends of the two vertical struts;
 c) a lower shin cuff attached at opposed ends to the distal ends of the two vertical struts; and
 d) a swing assist assembly containing at least one elastic member located on at least one of the hinge members, the at least one elastic member connected on a first end to the proximal half of each of the vertical struts and connected on a second end to the distal half of each of the vertical struts;
 e) one or more shin cuff elastic members connecting the lower shin cuff with either one or both of the two vertical struts;
 one or more interchangeable setting blocks, the one or more interchangeable setting blocks affecting the tension of the one or more shin cuff elastic members; and
 g) wherein the lower shin cuff is attached at opposite ends to each of the distal portions of the two vertical struts by a pair of pivots, each pivot of the pair of pivots located at the distal end portion of each of the two vertical struts.

10. The knee orthosis of claim 9, further comprising at least one air bladder employed along an inner surface of the one or both of the vertical struts.

11. The knee orthosis of claim 9 further comprising a plurality of air bladders employed along inner surfaces of one or both of the vertical struts, the air bladders configured to apply corrective and therapeutic force to the knee joint on both sides.

12. The knee orthosis of claim 9, wherein the one or more shin cuff elastic member members is a looped elastic cord.

13. A knee orthosis device comprising:
 a) two vertical struts, positioned on opposing sides of a knee joint in a generally parallel relationship, each vertical strut having a proximal half and a distal half, the proximal half having a first end and second end, the distal half having a third end and forth end;
 b) each vertical strut having a hinge member, the hinge member connecting the second and third ends;
 c) opposed ends of an upper thigh cuff attached to each of the vertical struts at a point adjacent to the first ends of each vertical struts;
 d) opposed ends of a lower shin cuff attached to each of the vertical struts at a point adjacent to the fourth ends of the each vertical strut; and
 e) at least one elastic member connected at one end to the proximal half of each of the vertical struts and connected on a second end to the distal half of each of the vertical struts;
 f) one or more shin cuff elastic members connecting the shin cuff with one or both of the vertical struts;
 g) one or more interchangeable setting blocks, the one or more interchangeable setting blocks affecting the tension of the one or more shin cuff elastic members; and
 h) wherein the lower shin cuff is rotatable about a pair of pivots, thereby allowing an inner surface of the shin cuff to remain substantially parallel to a shin of a person wearing the knee orthosis during motion.

14. The knee orthosis of claim 13 further comprising a plurality of adjustable air bladders employed along an inner surface of one or both of the vertical struts, the adjustable air bladders configured to apply varying amounts of corrective and therapeutic force to the knee joint on both sides, the varying amounts of force adjustable based on air pressure.

* * * * *